Figure 1:
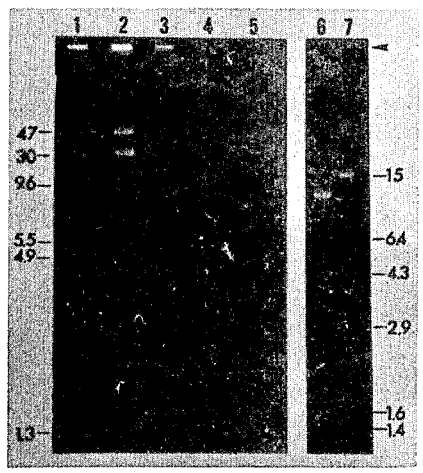

United States Patent [19]

Schnepf et al.

[11] 4,448,885

[45] May 15, 1984

[54] BACILLUS THURINGIENSIS CRYSTAL PROTEIN IN *ESCHERICHIA COLI*

[75] Inventors: H. Ernest Schnepf; Helen R. Whiteley, both of Seattle, Wash.

[73] Assignee: Board of the Regents of the University of Washington, Seattle, Wash.

[21] Appl. No.: 257,963

[22] Filed: Apr. 27, 1981

[51] Int. Cl.³ .................... C12N 1/20; C12N 15/00; C12N 1/00; C12P 21/00

[52] U.S. Cl. .................................. 435/253; 435/68; 435/172.3; 435/317

[58] Field of Search ................ 435/253, 317, 68, 172; 424/93

[56] References Cited

PUBLICATIONS

Losick et al., Cell 25, 582 (1981).
Moran et al., Cell 25, 783 (1981).
Rajalakshmi, Biological Abstr., 72:19676, J. Indian Sci. Sect. C Biol. Sci. 62, 21 (1980).
Gonzalez et al., Plasmid 3, 92 (1980) in Chem. Abstr. 93:65801.
Bolivar et al., Gene 2, 95 (1977).
Lilley et al., "Purification of the Insecticidal Toxin in Crystals of *Bacillus thuringiensis*", J. Gen. Micriobiol. 118:1–11 (1980).
Blair et al., "Isolation of Supercoiled Colicinogenic Factor $E_1$DNA Sensitive to Ribonuclease and Alkali", PNAS US69:2518–2522 (1972).
Erlich et al., "A Sensitive Radioimmunoassay for Detecting Products Translated from Cloned DNA Fragments", Cell 13:681–689 (1978).
Maniatis et al., "Nucleotide Sequence of the Rightward Operator of Phage λ", PNAS US 72:1184–1188 (1975).
White & Nester, "Hairy Root: Plasmid Encodes Virulence Traits in *Agrobacterium rhizogenes*" J. Bact. 141:1134–1141 (1980).
Meyers et al., J. Bact., 127:1529–1537 (1976).
Wahl et al., PNAS US 76:3583–3687 (1979).
Thomashow, et al., "Integration and Organization of Ti Plasmid Sequences in Crown Gall Tumors", Cell 19:729–739 (1980).
Henning et al., "Radioimmunological Screening Method for Specific Membrane Proteins", Anal. Biochem., 97:153–157 (1979).
Renart, et al., PNAS US, 76:3116–3120 (1979).
Cleveland et al., J. Biol. Chem., 252:1102–1106 (1977).
Bradford, Marion M., Anal. Biochem., 72:248–254 (1976).

*Primary Examiner*—Esther M. Kepplinger
*Assistant Examiner*—James Martinell
*Attorney, Agent, or Firm*—Fitch, Even, Tabin & Flannery

[57] ABSTRACT

Expression of the crystal protein of *Bacillus thuringiensis* in *E. coli* is described by use of plasmids containing heterologous DNA coding for the crystal protein. Genetically engineered bacterial host strains transformed by the recombinant plasmids of the invention express *B. thuringiensis* crystal proteins.

6 Claims, 3 Drawing Figures

BACILLUS THURINGIENSIS CRYSTAL PROTEIN IN ESCHERICHIA COLI

The U.S. government has rights in this invention pursuant to a grant awarded by The Department of Health and Human Services.

This invention relates generally to the production of substances for the control of insects injurious to certain plants. More particularly, the invention relates to an improved means for producing substances toxic to larvae of the tobacco hornworm *Manduca sexta* and related species.

The crystals made by *B. thuringiensis* are toxic to the larvae of a number of lepidopteran insects. Preparations containing such crystals are used commercially as a highly selective biological insecticide. However, problems connected with the use of such insecticides, together with relatively high manufacturing costs, have made it difficult, in many cases, for such insecticides to compete effectively with other commercially available products.

It is an object of this invention to provide an improved means of manufacturing *B. thuringiensis* crystals.

Other objects of the invention will become apparent to those skilled in the art from the following description, taken in connection with the accompanying drawings wherein:

FIG. 1 is an agarose gel analysis of plasmid DNAs and marker DNA fragments comprising a photograph of 0.7% (lanes 1-5) and 0.35% (lanes 6 and 7) agarose slab gels stained with ethidium bromide.

Figure 2:
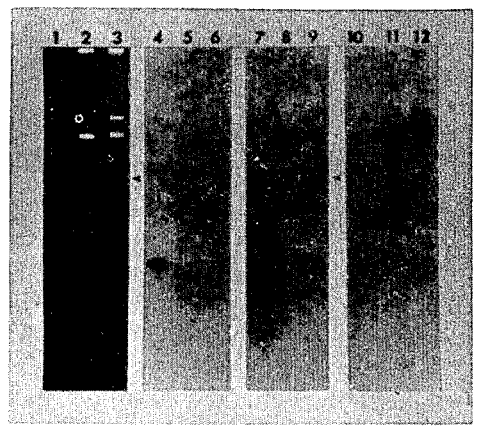
Figure 3:
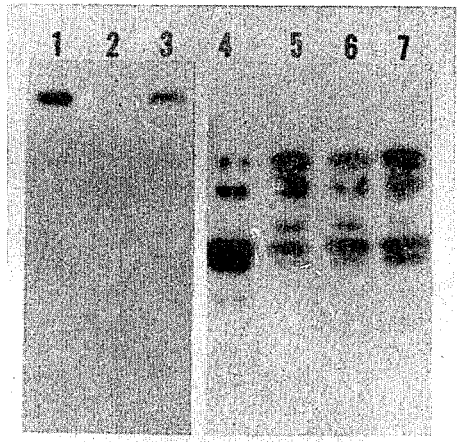

FIG. 2 is a hybridization analysis of plasmid DNAs transferred to nitrocellulose comprising a photograph of 0.7% ethidium bromide stained agarose gel (lanes 1-3) and autoradiograms of $^{32}$P labeled plasmids (lanes 4-12); and FIG. 3 is a radioimmune assay of crystal protein and proteins produced by strain ES12 before and after digestion with trypsin.

Very generally, the plasmids of the invention are capable of replication in a bacterial strain. The plasmids contain expressible DNA encoding for the crystal protein *B. thuringiensis*. In another form, the invention comprises a bacterial strain which contains such a plasmid.

Sporulating cells of *B. thuringiensis* produce intracellular protein crystals which are toxic to the larvae of a number of lepidopteran insects. Preparations containing crystals and spores made from *B. thuringiensis* are used commercially as a highly selective biological insecticide.

In accordance with a preferred form of the invention, the known cloning vector plasmid pBR322 (ATCC 37017) is combined with plasmid fragments obtained from plasmids harbored by strains of *B. thuringiensis*. The latter plasmids are believed to be responsible for the production of the crystal protein in *B. thuringiensis*. These plasmids were obtained from *B. thuringiensis* variation *Kurstaki* HD-1 (NRRL B3792) and range in molecular mass from 47 to 1.32 megadaltons as shown in lane 1 of FIG. 1, which is the total plasmid complement from this strain. Two fractions were obtained (lanes 2 and 3 of FIG. 1), one (lane 2) containing the 47 and 30 megadalton plasmids of *B. thuringiensis* (molecular weight $\times 10^6$ shown on left) and the second containing four smaller plasmids of 4.9, 5.2, 5.5 and 9.6 megadaltons (lane 3).

A preferred recombinant plasmid of the invention, designated pES1, is shown in lane 4 of FIG. 1 in which the gel analysis of the plasmid may be compared with pBR322, shown in lane 5. After digestion by an enzyme which cuts the plasmid once, the linearized plasmid had a mobility corresponding to ca. $11 \times 10^6$ $M_r$ when compared to Hind III digested lambda DNA (lanes 6 and 7 of FIG. 1). Molecular weights ($\times 10^{-6}$) on the right refer to the Hind III digest of lambda DNA. The arrow on the right in FIG. 1 marks the origin for lanes 6 and 7.

The plasmid pES1 demonstrated evidence that it is a recombinant plasmid consisting of vector and target DNA as shown in FIG. 2. The plasmid pES1 contains substantial homology with DNA from the plasmid pBR322 as well as DNA homologous to both the large plasmids of *B. thuringiensis*. In FIG. 2, lanes 1-3 are a photograph of a 0.7% ethidium bromide-stained agarose gel: (1) BamH 1 digested pBR322 DNA; (2) total plasmid complement of *B. thuringiensis* and (3) "large plasmid fraction" from *B. thuringiensis*. Lanes 4-6 are an autoradiogram of $^{32}$P-labeled pBR322 DNA hybridized with: (4) BamH 1 digested pBR322 DNA; (5) total plasmid complement and (6) "large plasmid friction" from *B. thuringiensis*. Lanes 7-9 are an autoradiogram of $^{32}$P-labeled pES1 DNA hybridized with: (7) BamH 1 digested pBR322; (8) total plasmid complement and (9) "large plasmid fraction" from *B. thuringiensis*. Lanes 10-12 are an autoradiogram of $^{32}$P-labeled total *B. thuringiensis*; plasmid DNA hybridized with: (10) BamH 1 digested pBR322 DNA; (11) total plasmid complement and (12) "large plasmid fraction" from *B. thuringiensis*.

FIG. 3 is a radioimmune assay of crystal protein produced by ES12 before and after digestion with trypsin. Autoradiograms of a solid-phase radioimmune assay for polypeptides are shown in lanes 1-3 of FIG. 3. Tryptic polypeptide fragments are shown in lanes 4-7 of FIG. 3. These fragments react with anti-crystal antibody following NaDodSo$_4$/polyacrylamide gel electrophoresis. Lane 1 is 1 $\mu$g *B. thuringiensis* crystal protein. Lane 2 is 100 $\mu$g *E. coli* HB101 (pBR322) protein extract. Lane 3 is 100 $\mu$g ES12 protein extract. Lane 4 is derived from dissolved *B. thuringiensis* crystals reacted with 5% (wt/wt) trypsin at pH 10 for 3 hours at room temperature. Lanes 5-7 are ES12 extract reacted with: (5) 2% (wt/wt) trypsin; (6) 4% (wt/wt) trypsin; and (7) 6% (wt/wt) trypsin at pH 10 for 3 hours at room temperature.

Lanes 1-3 of FIG. 3 show that the antigen made by ES12, which reacted with crystal protein antibodies, had the same electrophoretic mobility as the *B. thuringiensis* crystal protein. Dissolved *B. thuringiensis* crystals and cell extracts of HB101 (pBR322) and ES12 were electrophoresed on a NaDodSO$_4$/polyacrylamide gel and reacted with anti-crystal antibody and $^{125}$I-Protein A after transfer to nitrocellulose. The ES12 extract (lane 3 of FIG. 3) contained a polypeptide antigen having the same (or very similar) electrophoretic mobility to the dissolved *B. thuringiensis* crystals (lane 1 of FIG. 3). This polypeptide antigen was missing from a similar extract of HB101 (pBR322) (lane 2 of FIG. 3) and was not detected when pre-immune serum was substituted for anti-crystal antibody, or when $^{125}$I-Protein A was used without prior antibody treatment (data not shown).

Comparison of the bands shown in FIG. 3 (1 μg crystal protein in lane 1) with the total amount of protein applied to lane 3 (100 μg) indicates that the crystal protein antigen accounts for a small amount of the protein (1% or less) in ES12. When the radioimmune detection of polypeptide was used to monitor the fractionation of ES12 extracts it was found that a reducing agent plus a denaturant or an alkaline pH was required to solubilize the crystal protein antigen. These conditions are also required to solubilize B. thuringiensis crystals.

It has been reported by Lilley et al, *J. Gen. Microbiol.* 118:1–11 (1980) that the crystal protein can be digested by a number of proteases at pH 10 to produce primarily a single polypeptide. Lanes 4–7 of FIG. 3 show the results of an experiment where dissolved *B. thuringiensis* crystals and an eluate from the particulate fraction of ES12 were subjected to partial digestion at pH 10 with the indicated amounts of trypsin. As seen in lanes 5, 6, and 7 of FIG. 3, digestion of the ES12 extract with increasing amounts of trypsin yielded a pattern (lane 7 of FIG. 3) which was similar to the pattern produced by trypsin digestion of the crystal protein of *B. thuringiensis* (lane 4 of FIG. 3). Qualitatively the patterns of the bands generated from the two preparations were similar. The quantitative (and minor qualitative) differences may reflect a less efficient digestion of the crystal protein antigen in ES12 extracts due to the presence of numerous other polypeptide species.

The larger number of polypeptides produced by trypsin digestion of the crystal protein in these experiments as opposed to the number reported by Lilley et al, supra, may be due to differences in the conditions of trypsin treatment. Similar experiments using subtilisin also showed agreement in the electrophoretic mobilities of the bands produced from the crystal protein of *B. thuringiensis* and the bands produced by digesting extracts of ES12 (data not shown).

Evidence that extracts of ES12 contain a biological activity similar to the crystal protein of *B. thuringiensis* was obtained by assaying for insect toxicity. Extracts of particulate fractions obtained from *E. coli* HB101 (pBR322) and ES12 were mixed with feed meal supplied to neonate caterpillars of the tobacco hornworm *Manduca sexta.* Neonate larvae of the *Manduca sexta* were supplied by Drs. J. Truman and L. Riddiford, Department of Zoology, University of Washington. Extracts were prepared as described above from 8 liters of the appropriate *E. coli* strains; 6–8 mls of extract were mixed with 50 ml of molten agar-based diet and quickly poured to give a shallow layer. Strips of the solidified diet were placed in glass vials (3–4 ml/vial) with one neonate larva for 10 days at room temperature.

The results indicated that the extracts of the recombinant strain were toxic to caterpillars. The 15 larvae exposed to the ES12 extracts did not complete the first instar before death. An equivalent amount of extract from *E. coli* HB101 (pBR322) had no noticeable effect on the growth and development of 15 larvae through at least the third instar when compared to larvae grown on feed meal without any extract added. Identical results were obtained when this experiment was repeated with another set of *E. coli* extracts. The minimal amount of extract of ES12 required to kill the caterpillar larvae has not yet been determined. Assuming that the crystal protein antigen in the ES12 extracts was 0.5–1% of the total protein, then the feed meal prepared with the extract from ES12 contained 12–25 μg crystal protein per ml whereas a concentration of 2 μg/ml of pure crystal protein is sufficient to achieve 100% killing of the larvae.

The resulting strain of *E. coli,* ES12, carries a recombinant plasmid and produces a protein antigen that reacts with antibodies specific for the crystal protein of *B. thuringiensis.* This is confirmed by the above described tests wherein the recombinant plasmid isolated from this strain, pES1, simultaneously transforms cultures of *E. coli* strain HB101 to both ampicillin resistance and the production of the crystal protein antigen, whereas the plasmid vector pBR322 transforms HB101 to ampicillin and tetracycline resistance but no crystal antigen can be detected. Test results indicate that the DNA insert of the recombinant plasmid pES1 encodes the ability to make a polypeptide possessing properties similar to those of the crystal protein of *B. thuringiensis.* In fact, the results strongly suggest that the DNA insert of pES1 encodes the gene for the crystal protein of *B. thuringiensis* and that this gene is expressed in a biologically active form in *E. coli.* Preparations made from this new strain ES12 may therefore be used as insecticides for appropriate cases.

In constructing recombinant plasmids according to the invention, the following detailed procedures were followed. These procedures are given only by way of example and are not intended to limit the scope of the claims herein. The two separated plasmid fractions obtained from *B. thuringiensis* var. *Kurstaki* strain HD-1 (NRRL B3792) were digested with varying dilutions of Sau 3AI. This was monitored by agarose gel electrophoresis. To generate a source of inserts, the large plasmid fraction was digested with the minimum amount of enzyme needed to convert all the closed covalent circular molecules to the linear form. Restriction endonucleases Sal I, Hind III, BamH 1 and Sau 3AI were used as recommended by the manufacturer (New England Biolabs). This resulted in fragments with an average size greater than 10 megadaltons. For the small plasmid fraction, an amount of Sau 3AI was used which left some closed covalent circular molecules, but produced few linear fragments under $2\times10^6$ $M_r$ in size.

Each fraction was then ligated to pBR322 (ATCC 37017) opened by digestion with the restriction enzyme BamH 1. Plasmid pBR322 was isolated from *E. coli* strain HB101 (pBR322) as outlined by Blair et al *Proc. Nat. Acad. Sci. U.S.A.* 69:2518–2522 (1972). DNA fragments (3 μg of *B. thuringiensis* plasmid DNA and 0.15 μg of pBR322 DNA in a volume of 10 μl) were ligated as described for cohesive ends by Maniatis et al in *Cell* 15:667–701 (1978).

Recombinants were then screened and selected. Staphylococcus Protein A (Pharmacia) was labeled with $^{125}I$ (Amersham) using chloramine T as described by Erlich et al, *Cell* 13:681–689 (1978). The DNA polymerase I-catalysed fill-in reaction described by Maniatis et al *PNAS* 72:1184–1188 (1975) was used to label DNA fragments of Sau 3AI digests with [α-=P]dCTP (Amersham).

Plasmids were obtained from *B. thuringiensis* var. *Kurstaki* HD-1 (kindly provided by Dr. Lee A. Bulla, Jr.) according to the method for plasmid screening of White and Nester *J. Bact.* 141:1134–1141 (1980). *B. thuringiensis* var. *Kurstaki* HD-1 is on deposit with the NRRL, Peoria, Ill. and is available to anyone without restriction. It carries NRRL Number B3792. All plasmid preparations were additionally purified by centrifugation in cesium chloride-ethidium bromide gradients.

Samples (100 μg DNA per gradient) for cloning experiments were fractionated by centrifugation through 5–25% sucrose gradients for 2.5 hours at 35,000 RPM in an International B-60 centrifuge using the SB-283 rotor. Electrophoresis in agarose gels was used to analyze plasmid DNAs as described by Meyers et al, *J. Bact.* 127:1529–1537 (1976). Fragments of the plasmids were produced by digestion of DNA with restriction enzymes as is known in the art. Hybridization to plasmid DNAs was performed after partial depurination as described by Wahl et al, *Proc. Nat. Acad. Sci. U.S.A.* 76:3683–3687 (1979) and transfer of DNA from gels to nitrocellulose was done as described by Thomashow et al *Cell* 19:729–739 (1980).

The recombinant plasmids thus produced were then transformed into *E. coli*. Transformation was carried out as described by known procedures and transformants were selected on media containing 100 μg/ml ampicillin. Since cloning was performed by insertion of passenger DNA into the BamH I site of pBR322, which is located in a gene coding for tetracycline resistance, ampicillin resistant transformants were screened for sensitivity to tetracycline (25 μg/ml). Colonies resistant to ampicillin but sensitive to tetracycline were presumed to contain inserts.

Those transformed colonies presumed to carry *B. thuringiensis* DNA inserts were then screened for the production of crystal protein antigen using antibodies and $^{125}$I-Protein A. To prepare antibodies to the crystals, the crystals were first purified from sporulated cultures of *B. thuringiensis* grown in modified G medium (28) by four successive centrifugations in Renograffin (Squibb) gradients. Contamination with spores was estimated at less than 0.1% by phase microscopy. Solubilized crystals were electrophoresed on preparative 10% polyacrylamide slab gels containing NaDodSO$_4$, and the portion of the gel containing the major crystal protein polypeptide was sliced from the gel, crushed, mixed with an equal amount of Freund's Complete Adjuvant and used to immunize rabbits. The immunoglobulin G fraction was purified from the serum of the immunized rabbits. The immunoglobulin G fraction was purified from the serum of the immunized rabbits by precipitation with ammonium sulfate and chromatograph of DEAE cellulose and analyzed by Ouchterlony immunodiffusion, as is known in the art.

To screen by detection of antigens, colonies were first transferred from agar plates to filter paper and denatured with phenol-chloroform-heptane and chloroform-methanol as described by Henning et al *Anal. Biochem.* 97:153–157 (1979). The filters were soaked in 1% bovine serum albumen (Sigma, fraction V) and incubated with antibody and $^{125}$I-Protein A (Renart et al, *Proc. Nat. Acad. Sci. USA* 76:3116–3120; 1979). Colonies containing material capable of reacting with the crystal protein antibodies were detected by autoradiography. The concentrations of antibody ($10^{-3}$ to $10^{-4}$ dilution) and $^{125}$I-Protein A (0.2 to $1 \times 10^6$ cpm) were varied to obtain conditions permitting the detection of 5 ng crystal protein in 1 μl spotted on a filter while colonies of *E. coli* HB101 (pBR322) were either unreactive or appeared light against a grey background. Protein samples were electrophoresed on 10% NaDodSO$_4$/-polyacrylamide slab gels, transferred electrophoretically to nitrocellulose, and incubated with antibody ($5 \times 10^{-3}$ dilution) and $^{125}$I-Protein A ($6 \times 10^5$ cpm) in accordance with known procedures. The reaction of transferred peptides with antibody and $^{125}$I-Protein A was detected by radioautography.

Cells grown for 16 hours in L broth containing 100 μg/ml ampicillin were harvested by centrifugation, suspended in 0.1 M Tris buffer at pH 7.0, 1 mM EDTA, 200 μg/ml phenylmethylsulfonyl fluoride and disrupted by sonication. Insoluble material, obtained by centrifugation of the sonicates at 100,000×g for 30 minutes, was thoroughly suspended in 4 M urea, 0.285 M 2-mercaptoethanol, 0.05 M NaHCO$_3$, pH 9.5 and clarified by centrifugation. The supernatant fraction was dialysed twice against 100 volumes of 3 mM NaHCO$_3$, 7 mM 2-mercaptoethanol, pH 9.5, for a total of 16 hours at 4° C. and centrifuged at 100,000×g for 30 minutes. Ammonium sulfate was added to the supernatant fraction to give 25% saturation, and the precipitated material was pelleted, dissolved in a small volume of 4 M urea, 0.285 M 2-mercaptoethanol, 0.05 M NaHCO$_3$, pH 9.5, and dialysed against 0.05 M Tris buffer pH 7.4 for insect toxicity assays or for electrophoretic analysis. For proteolysis with subtilisin or trypsin, the samples were prepared as above substituting 0.05 M cyclohexylaminoethane sulfonic acid (CHES), pH 10.0, 0.285 M 2-mercaptoethanol for pH 9.5 urea buffer; final dialysis was against 0.01 M CHES buffer, pH 10.0. For trypsin digestion, 0.01 M CHES was used as the buffer and digestion was carried out at room temperature during dialysis against that buffer; digestion with subtilisin was performed according to Cleveland et al, *J. Biol. Chem.* 252:1102–1106 (1977). The reactions were stopped by boiling the samples in electrophoresis sample buffer and polypeptides capable of reacting with antibody to the crystal protein were detected using $^{125}$I-Protein A and radioautography as described above. Protein concentrations were determined according to Bradford, *Anal. Biochem.* 72:248–254 (1976).

By way of further example, recombinant plasmids were constructed incorporating crystal genes from *B. thuringiensis* var. *Kurstaki* strain HD-73. *B. thuringiensis* var. *Kurstaki* strain HD-73 is also on deposit with the NRRL Peoria, Ill. and is available to anyone without restriction. It carries NRRL Number B4488. The procedures in accomplishing this were essentially identical with those set forth above. The crystal protein produced has toxicity characteristics similar to those described for crystals coded by the genes from *B. thuringiensis* strain HD-1 described earlier.

It may be seen therefore that, in accordance with the invention, crystal protein of *B. thuringiensis* is produced in a recombinant strain.

Various modifications of the invention in addition to those shown and described herein will become apparent to those skilled in the art for the foregoing description and accompanying drawings. Such modifications are intended to fall within the scope of the appended claims.

What is claimed is:

1. An *Excherichia coli* bacterial strain transformed to express a polypeptide of 130,000 Mr having the immunological properties of crystal protein of *Bacillus thuringiensis*.

2. A hybrid recombinant plasmid capable of replication in an *Escherichia coli* bacterial host species, said plasmid containing expressible heterologous DNA coding for a polypeptide of 130,000 Mr which has the immunological properties of crystal protein of *Bacillus thuringiensis*, said plasmid further including an expression mechanism for said heterologous DNA which is recognized by the host species' system.

3. A plasmid according to claim 2 comprising a portion derived from plasmid pBR322 (ATCC 37017).

4. A hybrid *Escherichia coli* bacterial strain containing a plasmid in accordance with claim 2.

5. A hybrid recombinant plasmid according to claim 2 wherein said expressible heterologous DNA within the plasmid further comprises a DNA portion derived from plasmids of *Bacillus thuringiensis* having a molecular mass greater than $10 \times 10^6$ Mr.

6. A hybrid recombinant plasmid according to claim 2 wherein said expressible DNA comprises a DNA portion derived from plasmids from *Bacillus thuringiensis*, var. *kurstaki* HD-1 or *Bacillus thuringiensis*, var. *kurstaki* HD-73.

* * * * *